(12) United States Patent
Panin

(10) Patent No.: US 9,622,949 B2
(45) Date of Patent: Apr. 18, 2017

(54) FORMULATION FOR PERSONAL HYGIENE

(71) Applicant: BIO.LO.GA. S.R.L., Conegliano (Treviso) (IT)

(72) Inventor: Giorgio Panin, Rovigo (IT)

(73) Assignee: BIO.LO.GA. S.R.L, Conegliano (Treviso) (IT)

( * ) Notice: Subject to any disclaimer, the term of this patent is extended or adjusted under 35 U.S.C. 154(b) by 0 days.

(21) Appl. No.: 15/126,521

(22) PCT Filed: Mar. 20, 2015

(86) PCT No.: PCT/EP2015/055927
§ 371 (c)(1),
(2) Date: Sep. 15, 2016

(87) PCT Pub. No.: WO2015/144583
PCT Pub. Date: Oct. 1, 2015

(65) Prior Publication Data
US 2017/0079894 A1    Mar. 23, 2017

(30) Foreign Application Priority Data
Mar. 24, 2014  (IT) .................................. MI14A0495

(51) Int. Cl.
| | | |
|---|---|---|
| *A61K 8/97* | (2006.01) | |
| *A61K 8/06* | (2006.01) | |
| *A61K 8/37* | (2006.01) | |
| *A61K 8/67* | (2006.01) | |
| *A61K 8/73* | (2006.01) | |
| *A61Q 19/10* | (2006.01) | |

(52) U.S. Cl.
CPC ................ *A61K 8/062* (2013.01); *A61K 8/37* (2013.01); *A61K 8/678* (2013.01); *A61K 8/73* (2013.01); *A61K 8/97* (2013.01); *A61Q 19/10* (2013.01)

(58) Field of Classification Search
None
See application file for complete search history.

(56) References Cited

U.S. PATENT DOCUMENTS

2007/0269525 A1* 11/2007 Gondek ................ A61K 8/042
424/502

FOREIGN PATENT DOCUMENTS

WO    2011083401 A2    7/2011

OTHER PUBLICATIONS

"Tea Tree Oil Mask", Database GNPD Mintel, 2010, XP002733809, Database accession No. 131629. (2 pages).
Carson et al., "*Melaleuca alternifolia* (Tea Tree) Oil: a Review of Antimicrobial and Other Medicinal Properties", Clinical Microbiology Reviews, 2006, vol. 19, No. 1, pp. 50-62.
"CMD Teebaumol Korperlotion",Biovio Naturkosmetik & Naturkost, 2014, XP002733810, Retrieved from the Internet: URL:http://www.biovio.de/Naturkosmetik/Koerperpflege/Bodylotion-1252/CMD-TeebaumoelkbA    Koerperlotion-200-ml.html [retrieved on Dec. 15, 2014].
International Search Report for International Application No. PCT/EP2015/055927 (Jul. 15, 2015)(4 pages).

* cited by examiner

*Primary Examiner* — Necholus Ogden, Jr.
(74) *Attorney, Agent, or Firm* — Lucas & Mercanti, LLP

(57) ABSTRACT

A formulation for personal hygiene in the form of O/W emulsion with a pH from 5.5 to 6.5, free of surfactants, comprising an emulsifier consisting of a fatty alcohol from 14 to 22 carbon atoms or of Glyceryl Stearate or a mixture thereof, Coco Caprylate and/or Coco Caprylate/Caprate, vitamin E or an ester thereof, and *Melaleuca alternifolia* oil.

18 Claims, No Drawings

FORMULATION FOR PERSONAL HYGIENE

CROSS-REFERENCE TO RELATED APPLICATIONS

This application is a 371 of PCT/EP2015/055927, filed Mar. 20, 2015, which claims the benefit of Italian Patent Application No. MI2014A000495, filed Mar. 24, 2014.

FIELD OF APPLICATION

The present invention relates to the field of the cosmetic and pharmaceutical industry.

In particular, the invention relates to a formulation for personal hygiene, provided with pronounced characteristics of tolerability, and suitable to the use as a co-adjuvant with soothing properties in case of diseases and inflammatory conditions of external genital organs.

BACKGROUND OF THE ART

The detergent formulations for personal hygiene have to be as delicate as possible, since they directly contact the mucous membranes of the genital system, which are very sensitive. Ideally, such formulations should not alter the natural microbial flora also in case of frequent washing, and they should preferably be free of alcohols and strong fragrances, in order to reduce the presence of potentially allergenic substances.

Personal hygiene detergents should not alter the natural acidity of the mucous membranes and must be formulated with ingredients which are not harsh or irritating. In the formulations of personal hygiene detergents available on the market, relatively delicate anionic surfactants are contained, such as sulfosuccinates, acylglutammates, or protein-fatty acid condensates, such as e.g. those derived from the condensation of coconut fatty acids and wheat or oat amino acids. The anionic surfactants are sometimes associated with amphoteric surfactants, such as betaines, or to non-ionic surfactants.

The known formulations sometimes contain long chain alcohols, oils and functional substances, such as plant extracts with a specific action. Among these, chamomile, calendula and lime tree extracts can be mentioned, with a refreshing and soothing activity, as well as thyme extract and *Melaleuca alternifolia* oil, with an antiseptic activity.

The known formulations for personal hygiene usually have a pH of about 3.5-4.0, corresponding to the vaginal pH.

Despite the measures mentioned above to use surfactants which are as much delicate as possible, to avoid the presence of irritating substances, and to maintain the vaginal pH, the formulations for personal hygiene that are currently commercially available are not completely satisfactory, especially when they are to be used by persons with more or less severe diseases of the external genital mucous membranes, in particular the vulva, for example, lichen and vulvites.

US 2007/269525 A1 discloses O/W gel compositions aimed at providing irritation free formulations, wherein such compositions include 0.05-5% by weight of a polymeric gel former selected from acrylic acid, acrylamide and homopolymers of acrylic acid and acrylamide, 0.1-10% by weight of a wax component, which may be i.a. a $C_{12-18}$ fatty alcohol or a partial glyceride, and 0.1-30% of an oil component. These compositions may contain "biogenic agents" including i.a. tocopherol and tocopherol acetate in an unspecified amount. The compositions according to US 2007/269525 A1 can be incorporated into body care formulations, the pH of which is not specified.

C. F. Carson et al.: "*Melaleuca alternifolia* (Tea Tree) Oil: a review of antimicrobial and other medicinal properties" Clinical Microbiology Reviews, vol. 19, no. 1, 1 Jan. 2006, pages 50-62, disclose the disinfectant and antiinflammatory properties of *Melaleuca alternifolia* oil.

SUMMARY OF THE INVENTION

The problem underlying the present invention has been to provide a new personal hygiene formulation which had a higher tolerability than that of the known formulations and which could be used even by persons with diseases of the external genital mucous membranes, without causing irritations or other problems, while performing and efficient soothing and antimicrobial action.

Such a problem has been solved by providing a formulation for personal hygiene in the form of O/W emulsion with a pH from 5.5 to 6.5, free of surfactants, except for comprising an emulsifier consisting of a fatty alcohol with 14 to 22 carbon atoms or of glyceryl monostearate (INCI name: Glyceryl Stearate) or a mixture thereof, which formulation further comprises Coco Caprylate and/or Coco Caprylate/Caprate, vitamin E or an ester thereof in an amount of 2.0 to 15% by weight on the total weight of the formulation, and *Melaleuca alternifolia* oil.

The above-mentioned fatty alcohol is preferably selected from the group consisting of lauryl alcohol, stearyl alcohol, myristyl alcohol, arachidyl alcohol, behenyl alcohol and cetylstearyl alcohol, the latter (Cetearyl Alcohol) being particularly preferred.

Vitamin E can be used as d-$\alpha$-tocopherol, as a mixture of the two enantiomers d and l of $\alpha$-tocopherol, as a mixture of other tocopherols ($\beta$, $\gamma$, $\delta$, $\epsilon$, $\zeta$, $\eta$) or as tocotrienols.

By ester of vitamin E is meant an ester of vitamin E as defined above with a carboxylic acid of formula R—COOH, wherein R is an alkyl radical having 1 to 19 carbon atoms, or an alkenyl or alkynyl radical having 2 to 19 carbon atoms.

Preferably, the above-mentioned ester is vitamin E acetate, n-propionate or linoleate.

The use of vitamin E acetate, particularly alpha-tocopheryl acetate, is particularly preferred.

The formulation preferably also contain jojoba oil (*Simmondsia Chinensis* Oil) and/or shea butter (Butyrospermum Parkii Butter).

Preferably, the formulation also comprises xanthan gum (Xanthan Gum).

Preferably, the formulation also comprises an organic acid selected from lactic, malic, citric and acetic acid. Particularly preferred is lactic acid, which is added in such an amount as to bring the pH of the formulation to 5.5-6.5, preferably to a pH of about 6.0.

Preferably, the formulation also comprises pentylene glycol (Pentylene Glycol).

Preferably, the formulation according to the present invention contains the following ingredients, in percentages by weight of the total weight of the formulation:

| | |
|---|---|
| Fatty alcohol with 14-22 carbon atoms | 1.5-5.0 |
| Glyceryl Stearate | 2.0-6.0 |
| Coco Caprylate | 15.0-25.0 |
| Vitamin E or ester thereof | 3.0-10.0 |
| *Melaleuca Alternifolia* Leaf Oil | 1.5-6.0 |

In an aspect thereof, the formulation may also contain 0.5-2.0% jojoba oil (*Simmondsia Chinensis* Oil) and/or 3.0-8.0% shea butter (Butyrospermum Parkii Butter).

The formulation may further contain 0.2-1.0% xanthan gum (Xanthan Gum).

The formulation may further contain from 0.05% to 0.25% lactic acid, to adjust the pH between 5.5 and 6.5, preferably at about 6.0.

The formulation may further contain from 3.0 to 8.0% pentylene glycol (Pentylene Glycol).

A particularly preferred formulation is the one set forth herein below (INCI names):

| | |
|---|---|
| Aqua | 51.00-58.00 |
| Coco Caprylate | 16.00-20.00 |
| Pentylene glycol | 4.00-6.00 |
| Glyceryl Stearate | 3.00-5.00 |
| Tocopheryl Acetate | 4.00-8.00 |
| *Butyrospermum Parkii* Butter | 4.00-7.00 |
| Cetearyl Alcohol | 2.00-4.00 |
| *Melaleuca Alternifolia* Leaf Oil | 2.00-5.00 |
| *Simmondsia Chinensis* Oil | 0.5-1.5 |
| Xanthan Gum | 0.3-0.8 |
| Lactic acid | 0.05-0.15 | pH = 5.8-6.2.

The formulation according to the present invention is provided with a high tolerability, by virtue of the absence of surfactants. The delicate detergent action of the formulation according to the present invention is provided by the emulsifiers contained therein, i.e., fatty alcohol with 14 to 22 carbon atoms and/or Glyceryl Stearate, which components have all strong affinity for the skin and the mucous membranes. The same affinity for the skin and mucous membranes is displayed by Coco Caprylate and Coco Caprylate/Caprate, which are provided with a considerable emollient action.

The application of the detergent formulation according to the present invention, by virtue of the absence of surfactants, does not even require the subsequent rinsing of the cleaned area. In such a case, the formulation may remain in contact with the skin and the mucous membranes, thus allowing the antimicrobial and soothing active ingredients contained therein to keep on exerting their action even after cleansing.

The antimicrobial action of the formulation according to the present invention is due to the presence therein of the tea tree or *Melaleuca alternifolia* essential oil. The latter component is rich in terpene derivatives, mainly oxygenated and non-oxygenated monoterpenes, sesquiterpenes and triterpene alcohols, which are responsible for the antimicrobial action.

In order to prevent any irritant effect related to the essential oils of the tea tree oil, the formulation according to the present invention provides for the presence of vitamin E or an ester thereof, in particular, tocopheryl acetate, having a considerable soothing and emollient action.

A further soothing and emollient effect can be obtained by incorporating in the formulation according to the present invention jojoba oil (*Simmondsia Chinensis* Oil) and/or shea butter.

The possible presence in the formulation according to the present invention, which is in the form of O/W emulsion, of xanthan gum, serves to stabilize the emulsion and to confer it a gel texture.

The possible presence of pentylene glycol also concurs to the stabilization of the formulation according to the present invention.

An important aspect of the formulation according to the present invention is its pH, which, as it has be seen, ranges between 5.5 and 6.5 and is preferably of about 6.0, unlike most of the detergent formulations for personal hygiene in the market, which have a pH of about 3.5-4.0.

A pH range centered around 6.0 has been selected because this is the pH value at the vulvar mucous membrane, which is the portion which is actually cleaned. Instead, the pH of 3.5-4.0 of most of the personal hygiene detergent formulations in the market corresponds to the pH of the vaginal mucous membrane, but the latter is not actually involved in the cleansing. The vaginal mucous membrane is reached only by vaginal douches, but in such a case, special vaginal formulations are used instead of detergent formulations.

On the contrary, a detergent formulation for personal hygiene with a pH of 3.5-4.0 has a risk to be irritant and cause burning sensations in the presence of vulvar lesions and reddening.

The pH of the formulation according to the present invention can be adjusted to a value of about 5.5-6.5 by the addition of a suitable amount of a physiologically compatible organic acid, and preferably lactic acid.

The absence of preservatives, colorants and perfumes in the formulation according to the present invention further concurs to its high tolerability.

DETAILED DESCRIPTION

The present invention will be now further described with reference to an example given by way of illustrative, non-limiting example.

EXAMPLE

| | |
|---|---|
| a) Aqua | 55.00 |
| b) Coco Caprylate | 17.00 |
| c) Pentylene glycol | 4.00 |
| d) Glyceryl Stearate SE | 3.00 |
| e) Tocopheryl Acetate | 6.50 |
| f) *Butyrospermum Parkii* Butter | 4.00 |
| g) Cetearyl Alcohol | 4.00 |
| h) *Melaleuca Alternifolia* Leaf Oil | 5.00 |
| i) *Simmondsia Chinensis* Oil | 0.50 |
| l) Xanthan Gum | 0.80 |
| m) 50% w/w lactic acid solution | 0.20 | pH = 6.0.

The formulation set forth above was prepared by weighing all the fatty phase (ingredients b, d, e, f, g, h, i). This phase is then brought to a liquid state by heating to 80° C. +/−2° C.

Xanthan gum (l) is added to the solution of water (a) and pentylene glycol (c) heated to 80° C. +/−2° C., under stirring, thus obtaining the aqueous phase. By means of a vacuum system, the liquid fatty phase is introduced by suction into the turboemulsifier containing the aqueous phase described above. The turboemulsifier is operated during about 30 minutes until a homogeneous emulsion is obtained.

Once the emulsion has been obtained, it is gradually brought back to room temperature; finally, the amount of lactic acid (m) necessary to obtain a pH=6 is added.

The formulation was tested by a group of 35 female subjects, with an age ranging between 17 and 80 years, with different vulvar diseases, including lichen (both hypertrophic and hypotrophic, with or without erosions or rhagades), acute forms of vulvitis (fungal forms, forms due to *Escheri-* chia coli, herpes, outcomes of diathermocoagulation for condylomatosis, outcomes of post-partum episiorraphy), outcomes of intervention on Bartholin's cyst. These subjects were asked to use only the formulation at issue for cleansing their private parts during a period of thirty days.

All 35 subjects participating in the test declared that they obtained a considerable improvement by using the formulation of the present example, noting a considerable reduction of the symptoms (e.g., burning sensation, reddening, itching) and in many cases the complete disappearance of such symptoms. No adverse reaction has been reported.

The invention claimed is:

1. A formulation for personal hygiene in the form of O/W emulsion with a pH from 5.5 to 6.5, free of surfactants except for comprising an emulsifier consisting of a fatty alcohol having from 14 to 22 carbon atoms or of Glyceryl Stearate or a mixture thereof, the formulation further comprising:
   Coco Caprylate and/or Coco Caprylate/Caprate;
   vitamin E or an ester thereof in an amount of 2.0 to 15% by weight on the total weight of the formulation; and
   *Melaleuca alternifolia* oil.

2. The formulation according to claim 1, wherein said fatty alcohol is selected from the group consisting of lauryl alcohol, stearyl alcohol, myristyl alcohol, arachidyl alcohol, behenyl alcohol and cetylstearyl alcohol.

3. The formulation according to claim 1, wherein said fatty alcohol is cetylstearyl alcohol (Cetearyl Alcohol).

4. The formulation according to claim 1, wherein said ester of vitamin E is an ester of tocopherol with a carboxylic acid of formula R—COOH, wherein R is an alkyl radical having 1 to 19 carbon atoms, or a alkenyl or alkynyl radical having 2 to 19 carbon atoms.

5. The formulation according to claim 4, wherein the ester of tocopherol is alpha-tocopheryl acetate, n-propionate or linoleate.

6. The formulation according to claim 1, further comprising jojoba oil (*Simmondsia Chinensis* Oil) and/or shea butter (Butyrospermum Parkii Butter).

7. The formulation according to claim 6, further comprising xanthan gum.

8. The formulation according to claim 1, further comprising an organic acid selected from the group consisting of lactic, malic, citric and acetic acid.

9. The formulation according to claim 1, further comprising pentylene glycol.

10. The formulation according to claim 1, containing the following ingredients, in percentages by weight of the total weight of the formulation:

| | |
|---|---|
| Fatty alcohol with 14-22 carbon atoms | 1.5-5.0 |
| Glyceryl Stearate | 2.0-6.0 |
| Coco Caprylate | 15.0-25.0 |
| Vitamin E or ester thereof | 3.0-10.0; and |
| *Melaleuca Alternifolia* Leaf Oil | 1.5-6.0. |

11. The formulation according to claim 9, further containing 0.5-2.0% of jojoba oil (*Simmondsia Chinensis* Oil) and/or 3.0-8.0% of shea butter (Butyrospermum Parkii Butter).

12. The formulation according to claim 11, further comprising 0.2-1.0% of xanthan gum.

13. The formulation according to claim 10, further comprising from 0.05% to 0.25% of lactic acid, to adjust the pH between 5.5 and 6.5.

14. The formulation of claim 13, wherein the pH is about 6.0.

15. The formulation of claim 12, further comprising from 0.05% to 0.25% of lactic acid, to adjust the pH between 5.5 and 6.5.

16. The formulation of claim 15, wherein the pH is about 6.0.

17. The formulation according to claim 10, further containing from 3.0 to 8.0% of pentylene glycol.

18. The formulation according to claim 1, having a pH of 5.8-6.2 and containing, in percentages by weight on the total weight of the formulation:

| | |
|---|---|
| Aqua | 51.00-58.00 |
| Coco Caprylate | 16.00-20.00 |
| Pentylene glycol | 4.00-6.00 |
| Glyceryl Stearate | 3.00-5.00 |
| Tocopheryl Acetate | 4.00-8.00 |
| *Butyrospermum Parkii* Butter | 4.00-7.00 |
| Cetearyl Alcohol | 2.00-4.00 |
| *Melaleuca Alternifolia* Leaf Oil | 2.00-5.00 |
| *Simmondsia Chinensis* Oil | 0.5-1.5 |
| Xanthan Gum | 0.3-0.8, and |
| Lactic acid | 0.05-0.15. |

* * * * *